United States Patent [19]

Bowman et al.

[11] Patent Number: 4,808,743

[45] Date of Patent: Feb. 28, 1989

[54] VINYL CHLOROFORMATES AND PREPARATION

[75] Inventors: Mark Bowman; Roy Olofson, both of State College, Pa.; Thierry Malfroot, Saintry-sur-Seine; Jean-Pierre Senet, Herbeauvilliers-Buthiers, both of France

[73] Assignee: Societe Nationale des Poudres et Explosifs, Cedex, France

[21] Appl. No.: 14,286

[22] Filed: Feb. 13, 1987

Related U.S. Application Data

[63] Continuation-in-part of Ser. No. 896,605, Aug. 13, 1986, Pat. No. 4,786,745.

[30] Foreign Application Priority Data

Aug. 23, 1985 [FR] France .................. 85 12652

[51] Int. Cl.$^4$ .................. C07C 68/02; C07C 69/07
[52] U.S. Cl. .................. 558/141; 558/142; 558/182; 558/280; 558/282; 558/283
[58] Field of Search .............. 558/141, 142, 182, 280, 558/283, 282

[56] References Cited

U.S. PATENT DOCUMENTS

| | | | |
|---|---|---|---|
| 2,221,275 | 11/1940 | Taylor | 560/229 |
| 3,080,405 | 3/1963 | Larsen et al. | 560/229 X |
| 3,213,062 | 10/1965 | Ellingboe et al. | 558/283 X |
| 3,823,171 | 7/1974 | Pittman et al. | 560/229 X |
| 4,487,781 | 12/1984 | Morisawa et al. | 560/229 X |
| 4,592,874 | 6/1986 | Cagnon et al. | 558/283 |
| 4,606,865 | 8/1986 | Palmer et al. | 558/283 |

OTHER PUBLICATIONS

Chemical Abstracts, vol. 72, No. 19, May 1970, Item 100243m.

*Primary Examiner*—Werren B. Lone
*Assistant Examiner*—Vera C. Clarke
*Attorney, Agent, or Firm*—Bucknam and Archer

[57] ABSTRACT

Vinyl chloroformates are described of formula

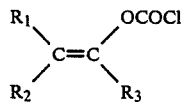

in which:
$R_1=R_2=$Cl, Br or a saturated 1-4 carbon atom alkyl or together they form a cycloaliphatic ring of 4-8 carbon atoms;
$R_3=$H when $R^1$ or $R^2=$alkyl; saturated alkyl of 1-4 carbon atoms or aryl;

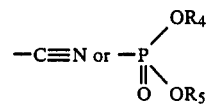

in which $R_4=R_5=$alkyl of 1-4 carbon atoms or $R_3$ forms with $R_2$ a $C_5$-$C_8$ ring which may have attached oxygen atoms. The process of preparation consists of reacting phosgene with the corresponding compounds containing alpha halogen and a carbonyl group. The products are very useful to obtain vinyl carbonates and carbamates.

12 Claims, No Drawings

VINYL CHLOROFORMATES AND PREPARATION

This application is a Continuation-in-Part of U.S. Ser. No. 896,605, filed Aug. 13, 1986, now U.S. Pat. No. 4,786,745.

The present invention relates to novel vinyl chloroformates, the process of preparation and their applications.

The chloroformates are intermediates in great demand in synthetic organic chemistry because they constitute an easy and little dangerous route for the preparation of two important families of compounds, the carbonates and carbamates, by reaction with an alcohol or a phenol in the first case, and by reaction with a primary or a secondary amine in the second case.

While chloroformates containing a saturated radical are easily accessible, the chloroformates containing an unsaturated chain are much less accessible and in fact only few compounds are known, particularly with respect to the vinyl chloroformates, that is, the chloroformates which have an unsaturation of the ethylenic type between the carbon atoms in positions 1 and 2.

Actually, there are known the vinyl chloroformates which have at least one atom of hydrogen in the beta position, such as vinyl chloroformate and 2-methyl-vinyl chloroformate which are described in U.S. Pat. No. 2,377,085. Also, isopropenyl chloroformate has been described in French Pat. No. 2 421 866 and a few other compounds are described in the publication "Synthesis of Enol Chloroformates" *J.O.C.*, 43, 752 (1978). The compounds 2,2-dihalogenovinyl chloroformates are described in the French patent application No. 85.12652 filed Aug. 23, 1985.

The number of vinyl chloroformates available actually to one skilled in the art is limited and this limitation reduces considerably the interest in the chloroformate route for the preparation of carbonates and carbamates containing a vinyl route, which, however, are compounds in great demand.

The object of the present invention is to provide novel vinyl chloroformates so that it is possible to enlarge the number of carbonates and carbamates having a vinyl group made through the chloroformate route. The invention, therefore, relates to novel compounds, vinyl chloroformates represented by the following structure:

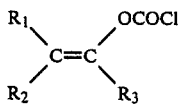

in which:

$R_1$ and $R_2$ are the same or different and are each an atom of chlorine, an atom of bromine or a saturated alkyl radical which may be linear or branched containing between 1 and 4 carbon atoms, the two radical $R_1$ and $R_2$ being capable of forming together with the carbon atom to which they are attached a cycloaliphatic ring containing between 4 and 8 carbon atoms.

$R_3$ is:

hydrogen when at least one of the radicals $R_1$ or $R_2$ is an alkyl radical, a saturated alkyl radical, linear or branched, containing between 1 and 4 carbon atoms. The radical $R_3$ also is capable of forming with the radical $R_2$ and the carbon atoms to which they are attached a cyclic hydrocarbon ring containing between 5 and 8 carbon atoms, which may be unsubstituted or substituted by oxygen atoms forming together with the carbon atoms of the ring a keto group, an aryl radical unsubstituted or substituted by alkyl groups and containing up to 8 carbon atoms, a cyano radical -C≡N, or a phosphonate radical of general formula:

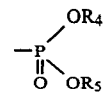

wherein $R_4$ and $R_5$ are the same or different, and each represents a saturated alkyl radical, linear or branched, containing between 1 and 4 carbon atoms.

The invention also relates to a process of preparation of the vinyl chloroformates which consists of reacting phosgene in a solvent in the presence of zinc, with an alpha-halo-carbonyl-containing compound of formula:

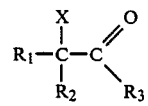

in which

X is a chlorine or bromine atom and $R_1$, $R_2$ and $R_3$ have the meaning indicated hereinabove.

Finally, the invention relates also to the application of vinyl chloroformates according to the invention in the preparation of vinyl carbonates and carbamates by reaction of the chloroformates with an hydroxyl-containing compound or a primary or secondary amine.

The method of preparation will be described hereinbelow.

The invention relates, therefore, to novel industrial products, vinyl chloroformates of formula:

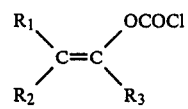

in which the radical $R_1$ and $R_2$ are the same or different and may be each a chlorine or a bromine atom, preferably a chlorine atom or a saturated alkyl radical, linear or branched, containing 1 to 4 carbon atoms and particularly a methyl or a propyl radical. The radicals $R_1$ and $R_2$ may also form together with the carbon atom to which they are attached a cycloaliphatic ring containing 4 to 8 carbon atoms, such as for instance the cyclohexyl ring.

The radical $R_3$ may have different meanings:

$R_3$ may be hydrogen when at least one of the radicals $R_1$ or $R_2$ is an alkyl radicals;

$R_3$ is a saturated alkyl radical, linear or branched, containing between 1 and 4 carbon atoms such as for instance the methyl radical. The radical $R_3$ may form together with $R_2$ and with the carbon atoms to which they are bound a cycloaliphatic ring containing between 5 and 8 carbon atoms which may be unsubstituted or substituted by oxygen atoms forming with the carbon atoms of the ring a keto function such as for instance a cyclohexenyl ring or oxo-cyclohexenyl.

R$_3$ may be an aryl radical which may be unsubstituted or substituted by alkyl groups and containing up to 8 carbon atoms and particularly the phenyl radical.

R$_3$ may designate a cyano group—C≡N.

R$_3$ may also represent a phosphonate radical of formula

in which R$_4$ and R$_5$ are the same or different and each represents a saturated alkyl radical, linear or branched, containing between 1 and 4 carbon atoms. The preferred phosphonates are the groups in which R$_4$ and R$_5$ are identical and represent either the methyl group or the ethyl group, that is the dimethylphosphonato and diethylphosphonato radicals.

As novel vinyl chloroformates one may mention 2-methyl-1-cyclohexenyl chloroformate; 1-methyl-2,2-dichlorovinyl chloroformate; 1-phenyl-2,2-dichlorovinyl chloroformate; 3-chlorocarbonyloxy-2-chloro-2-cyclohexene-1-one; 2-methyl-pentene-1-yl chloroformate; methylenyl cyclohexane chloroformate; 1-(O,O-dimetylphosphonato)-2-methyl-propene-1-yl chloroformate; 1-(O,O-diethylphosphonato)-2-methyl-propene-1-yl chloroformate; 2-chloropropene-1-yl chloroformate; 2-methyl-propene-1 yl chloroformate; 1-phenyl-2-methyl-propene-1-yl chloroformate; 1-cyano-2-methyl-propene-1-yl chloroformate.

The invention relates also to a process of preparation of the novel vinyl chloroformates.

Essentially, the process according to the invention consists of reacting in a solvent in the presence of zinc phosgene with a compound containing an alpha-halogen and a carbonyl group of formula:

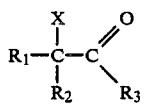

in which:

X is chlorine or bromine;

R$_1$, R$_2$ and R$_3$ are as defined hereinabove.

The compounds containing a carbonyl group are commercially available or may be easily synthesized from commercially available aldehydes and ketones. The reaction may be represented by the reaction scheme hereinbelow:

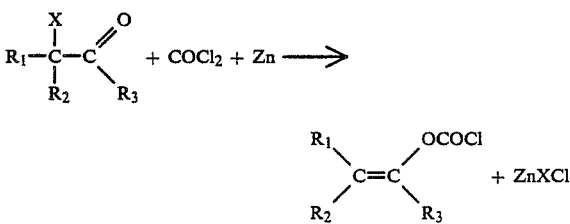

It is surprising to obtain unsaturated chloroformates because it has been known that metals such as zinc or Lewis acids for instance Zn Cl$_2$, cause the decomposition of the chloroformates be decarboxylation (M. Matzner et al, Chem. Review 64, pp. 668 and 670, 1964) such as for instance:

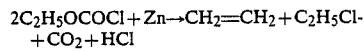

$2C_2H_5OCOCl + Zn \rightarrow CH_2=CH_2 + C_2H_5Cl + CO_2 + HCl$

It is also known that acid chlorides react with alpha-halogenated ketones in the presence of zinc to give diketones (Saitkulova et al., "Zhurnal Organicheskoi Khimii" Vol 22, No. 2, pp. 283—286, Feb. 1986).

Applicants have found, however, that in order for the reaction to proceed satisfactorily, it is essential that the radicals R$_1$ and R$_2$ have the meaning indicated hereinabove. In other words, the reaction does not proceed if R$_1$ or R$_2$ are hydrogen.

Specifically, reaction does not occur if one uses 2-chloroacetaldehyde, 2-chloro propanol or chloroacetone as the carbonyl containing compound. Therefore, the process does not permit to obtain the known vinyl chloroformate, 2-methylvinyl chloroformate and isopropenyl chloroformate.

The reaction is carried out in a solvent or in a mixture of solvents, preferably anhydrous. The solvents are selected linear ethers, cyclic ethers and esters, alone or in mixture with ethers. Tetrahydrofuran, dioxane, diethylether, dimethoxyethane, ethyl acetate, methyl acetate are particularly suitable.

According to an essential feature of the invention, the reaction is carried out in the presence of zinc, preferably as a powder. According to a preferred embodiment, powder zinc is first activated, for instance according to the methods set forth in Fieser and Fieser "Reagents for Organic Synthesis", New York, (1967), vol. 1, p. 1276. It is also possible to use zinc with copper in powder form prepared according to R. Wilkinson J. Chem. Soc. (1931), p. 3057.

There is used at least a stoichiometric quantity of zinc with respect to the molar quantity of the carbonyl compound and preferably a molar excess between 5% and 50%.

The molar quantity of phosgene used is at least equal to the molar quantity of the carbonyl compound, but preferably one uses an excess of phosgene, the total molar quantity of phosgene used being therefore between 1 and 2 molar amounts of the carbonyl compound being reacted.

The temperature of the reaction is in general between 0° C. and +60° C., preferably between +5° and +30° C.

The reaction time in general is between 30 minutes and a few hours.

After the reaction has ended, the solvents are removed, for instance by warming or under vacuum. If necessary, the zinc salts may be precipitated, for instance by addition of a mixture 2:1 of pentane and dioxane. The vinyl chloroformate may be removed by distillation, in general fractional distillation under vacuum.

The process according to the invention permits to obtain from easily accessible starting materials in a simple manner and in good yield the novel vinyl chloroformates.

The novel vinyl chloroformates may be used as monomer component in polymerisation of the vinyl group or may be intermediates in synthetic reactions.

The invention also relates to certain applications of the novel chloroformates. According to these applications, the vinyl chloroformates may be reacted with an hydroxylic compound or a primary or secondary amine to give vinyl carbonates or carbamates according to the reactions hereinbelow:

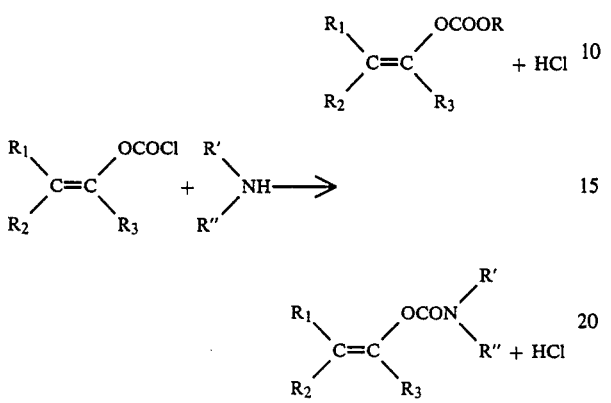

The experimental conditions of these reactions are the conventional conditions of the reactions of a chloroformate with an hydroxylic compound or an amine (Chemical Review 64, p. 651—657).

The vinyl carbonates and carbamates are well known in the art for their many applications in synthetic organic chemistry. The preparation and utilization of the vinyl carbonates are for instance described in U.S. Pat. No. 2,377,111 or French Application No. 86.12745. The preparation and utilization of the vinyl carbamates are described for instance in French pat. No. 2 533 561.

Due to the novel vinyl chloroformates according to the invention, the vinyl carbonates and carbamates are obtained much more easily than according to the more complex methods known in the art. The following examples illustrate the invention but are not intended to limit the invention.

EXAMPLE 1

Preparation of 2-methyl 1-cyclohexenyl chloroformate of formula

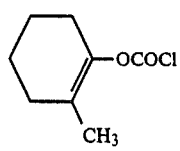

To a mixture of zinc powder (7.1 g equal to 0.11 mole) in 50 cc of ethyl acetate cooled in an ice bath, there is added 6.5 cc (0.09 mole) of phosgene. There is then added under stirring 11 grams (0.075 mole) of 2-chloro 2-methyl-cyclohexanone. After two hours, the mixture is filtered on a silica filter and then washed with 600 cc of dichloromethane. The mixture so obtained is concentrated and then purified by fractional distillation at a temperature between 80° C. and 82° C. under reduced pressure of 8 mm of mercury.

There is obtained 8.9 grams of 2-methyl 1-cyclohexenyl chloroformate of 99% purity by chromatography GC which corresponds to a yield of 67%.

The product so obtained has the following characteristics:

IR spectrum (in CCl$_4$): band at 1780 cm$^{-1}$, $^1$HNMR spectrum (in CDCl$_3$): δ ppm 2.4–1.9 (m, 7H), 1.8–1.4 (m, 4H), $^{13}$CNMR spectrum (in CDCl$_3$): δ ppm: 148.5 (C=O), 144.4 (=CO), 122.2 (=C), 30.0; 26.3; 23.0, 22.1 (CH$_2$); 15.9 (Me).

EXAMPLE 2

Preparation of 1-methyl 2,2 dichlorovinyl chloroformate of formula

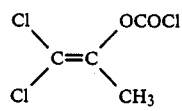

To a mixture of zinc powder (3.50 grams, that is, 0.054 mole) in 50 cc of ethyl acetate cooled in an ice bath, there is added 5 cc (0.070 mole) of phosgene. There is then added under stirring 3.69 grams (0.023 mole) of 1,1,1-trichloroacetone. After four hours, the solvent is removed under vacuum, and the product is extracted by washing with pentane (4×20 cc). The solution is concentrated and distilled at 56°–58° C. under reduced pressure of 17 mm of mercury.

There is obtained 1.0 gram of 1-methyl 2,2-dichlorovinyl chloroformate of 98% purity by chromatography GC which corresponds to a yield of 23%. The product obtained has the following characteristics:

IR spectrum(CCl$_4$): 1780 cm$^{-1}$, $^1$HNMR (CDCl$_3$): δppm: 2.17 (s)

$^{13}$CNMR (CDCl$_3$): δppm: 147.3 (C=O), 143.4 (=CO), 116.5 (CCl$_2$), 16.5 (Me).

EXAMPLE 3

Preparation of 1-phenyl-2,2-dichlorovinyl chloroformate of formula

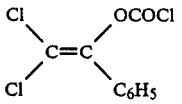

To a mixture of zinc powder (4.34 grams, that is, 0.066 mole) in 90 cc of methyl acetate cooled in an ice bath, there is added 6 cc (0.084 mole) of phosgene. There is then added in the course of two minutes under stirring 9.80 grams (0.044 mole) of 1,1,1-trichloro-acetophenone. The reaction starts immediately. After two hours, the solvent is removed under vacuum and the product is extracted by washing with pentane (5×50 cc). The solution so obtained is concentrated and distilled under reduced pressure of 0.4 mm of mercury. There is obtained 1-phenyl 2,2-dichlorovinyl chloroformate of 99% purity by chromatography GC which corresponds to a yield of 66%.

The product so obtained exhibits the following characteristics:

IR spectrum (CCl$_4$): 1795 cm$^{-1}$ 1680 cm$^{-1}$, $^1$HNMR (CDCl$_3$): δppm: 7.7–7,3 (m), $^{13}$CNMR (CDCl$_3$): δppm: 147.5 (C=O), 129.8 (=CO), 118.4 (CCl$_2$).

EXAMPLE 4

Preparation of 3-chlorocarbonyloxy 2-chloro 2-cyclohexene 1-one of formula

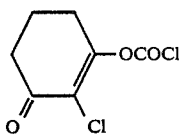

To a mixture of zinc powder (3.01 grams, that is, 0.046 mole) and phosgene (3.0 cc, that is, 0.042 mole) in 40 cc of ethyl acetate, there is added under stirring a solution of 6.64 grams (0.037 mole) of 2,2 dichloro 1,3 cyclohexanedione in 15 cc of ethyl acetate. The addition of the solution of the 2,2 dichloro 1,3-cyclohexanedione is carried out in three portions during a period of one hour. After two hours, the excess phosgene is removed under vacuum, 40 cc of a mixture 2:1 of pentane and dioxane is added, the mixture so obtained is filtered and the filtrate is concentrated under vacuum. The reaction product is extracted by washing with pentane (4×20 cc) and distilled at 108°–110° C. under reduced pressure of 0.8 mm of mercury. There is obtained in this manner 2.3 grams of 3-chlorocarbonyloxy 2-chloro 2-cyclohexene 1-one in a yield of 30%. The product so obtained has the following characteristics:

IR spectrum(CCl4): 1790 cm$^{-1}$, 1705 cm$^{-1}$, 1630 cm$^{-1}$, $^1$HNMR (CDCl$_3$): δppm: 2.9–2.5 (m, 4H), 2.4–1.8 (m, 2H).

It should be noted that the 3-chlorocarbonyloxy 2-chloro2-cyclohexene 1-one decomposes spontaneously in free air in room temperature, to give a white solid which has been identified as 2,3-dichloro 2-cyclohexene 1-one.

EXAMPLE 5

Preparation of 2-methyl penten-1-yl chloroformate of formula

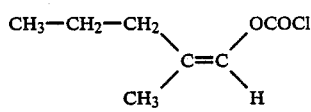

To a mixture of zinc powder (4.49 grams, that is 0.069 mole) and phosgene (7.0 cc, that is 0.098 mole) in 70 cc of ethyl acetate is added under stirring 9.16 grams (0.068 mole) of 2-chloro 2-methyl pentanal. The addition is made in three portions during a period of two hours. The reaction mixture is stirred for three hours and then there is added 70 cc of a mixture 2:1 of pentane and dioxane. After filtration, the filtrate is concentrated under vacuum and then purified by fractional distillation. There is obtained 3.0 grams of 2-methyl penten-1-yl chloroformate, which corresponds to a yield of 27%. The product exhibits the following characteristics:

boiling point: 67°–68° C. at 15 mm of mercury

IR spectrum (CCl4): 3090 cm$^{-1}$, 1780 cm$^{-1}$, 1680 cm$^{-1}$, $^1$HNMR (CDCl$_3$): δppm: 6.9–6.7 (m, 1H), 2.3–0.7 (m, 10H).

EXAMPLE 6

Preparation of methylenyl cyclohexane chloroformate of formula

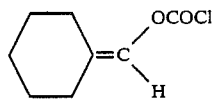

To a mixture of zinc powder (4.13 grams) and phosgene (5.5 cc) in 35 cc of ethyl acetate is added under stirring a solution of 7.0 grams (0.048 mole) of 1-chloro-cyclohexanecarboxyaldehyde in 15 cc of ethyl acetate. The addition is carried out in two portions during two hours. There is then added 1.02 grams of zinc powder and after stirring for three hours, 30 cc of a mixture 2:1 of pentane and dioxane is added. After filtration, the filtrate is concentrated under vacuum. Then 20 cc of pentane is added and the operations of filtration and concentration are repeated. Finally, distillation at 48°–50° C. is carried out under a reduced pressure of 0.7 mm mercury.

There is obtained 5.0 grams of cyclohexane methylenyl chloroformate which corresponds to a yield of 59%.

The product has the following characteristics:

IR spectrum (CCl4): 3090 cm$^{-1}$, 1775 cm$^{-1}$, 1680 cm$^{-1}$, $^1$HNMR (CDCl$_3$): δppm: 6.70: singlet 1H, 2.5–1.3 (m, 10H).

EXAMPLE 7

Preparation of 1-(O,O-dimethylphosphonato) 2-methyl propen-1-yl chloroformate of formula

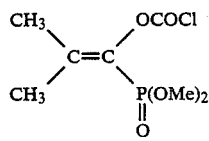

To a mixture of zinc powder (1.55 grams, that is 0.024 mole) in 25 cc of ethyl acetate, 2.5 cc (0.035 mole) of phosgene is added. Then 4.67 grams (0.018 mole) of 2-bromo 2-methyl propanoyl O,O-dimethylphosphonate is added. After 30 minutes the excess phosgene and solvent are removed under vacuum. The zinc salts are precipitated by addition of 25 cc of a mixture of 2:1 pentane and dioxane. The mixture is then filtered and the filtrate is concentrated under vacuum (0.7 mm of mercury) during two hours. The 2-methyl propen-1-yl (O,O-dimethyl phosphonato chloroformate is obtained in a yield of 83% determined by RMN$^1$H (solvent CDCl$_3$).

The product has the following characteristics:

IR spectrum (CCl4): 1780 cm$^{-1}$, $^1$HNMR (CDCl$_3$): δppm: 3.93 (d, 6H, J=12 Hz), 2.13 (d, 3H, J=3 Hz), 1.91 (d, 3H, J=3 Hz).

EXAMPLE 8

Preparation of 1-(O-O-diethylphosphonato) 2-methyl-propen-1-yl chloroformate of formula

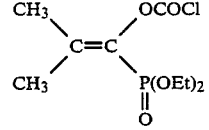

The compound 2-bromo 2-methyl propanoyl O,O-diethylphosphonate (4.21 grams, that is, 0.015 mole) is added to a stirred mixture of phosgene (2,0 cc, that is, 0.03 mole) and zinc powder (1.50 grams, that is 0.023 mole) in 25 cc of methyl acetate. Stirring is continued during three hours, then the excess phosgene is removed under reduced pressure and the mixture is filtered, the filtrate concentrated under vacuum. There is then added 25 cc of a mixture 2:1 of pentane and dioxane to cause the precipitation of the zinc salts. The mixture is again filtered and the filtrate is concentrated under vacuum overnight. The product 2-methyl propen-1-yl 1-(O,O-diethylphosphonato) chloroformate is obtained in a yield of 74% determined by RMN$_1$H (solvent CDCl$_3$).

The product exhibits the following characteristics:
IR spectrum (CCl$_4$): 1780 cm$^{-1}$ and 1640 cm$^{-1}$,
$^1$HNMR (CDCl$_3$): δppm: 4.34 (quintet, 4H, J=7 Hz), 2.13 (d, 3H, J=3 Hz), 1.89 (d, 3H, J=3 Hz), 1.40 (t, 6H, J=7 Hz).

EXAMPLE 9

Preparation of 2-chloro-propen-1-yl chloroformate of formula

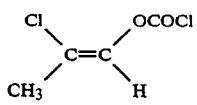

During a period of 2½ hours, 6 grams (0.09 mole), of zinc powder is added to a stirred solution of 2,2-dichloro propanol (10.7 grams, that is, 0.084 mole) and phosgene (10 cc, that is 0.14 mole) in 50 cc of methyl acetate. Stirring is continued for twenty minutes. The mixture is then filtered and purified by fractional distillation (68°–71° C. at 52 mm of mercury). The product 7.2 grams of 2-chloro-propen-1-yl chloroformate is obtained in a yield of 56%.

The product has the following characteristics:
IR spectrum (CCl$_4$): 3070 cm$^{-1}$, 1780 cm$^{-1}$,
$^1$HNMR (CDCl$_3$): δppm: 7.2–7.0 (m, 1H), 2.10 (d, 1.5H), 2.05 (d, 1.5H).

EXAMPLE 10

Preparation of 1-phenyl 2-methyl propen-1-yl chloroformate of formula

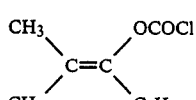

During a period of three hours, 3 grams (0.05 mole) of zinc powder is added to a stirred solution of 4.23 grams (0.023 mole) of alphachloroisobutyrophenone and 6.5 grams (0.07 mole) of phosgene in 20 cc ethyl acetate.

Stirring is continued overnight and the excess phosgene is removed under vacuum. The mixture is filtered and then purified by fractional distillation (54°–74° C. under a reduced pressure of 0.5 mm mercury). The product 1-phenyl 2-methyl propen-1-yl chloroformate has the following characteristics:
IR spectrum (CCl$_4$): 1780 cm$^{-1}$,
$^1$HNMR (CDCl$_3$): δppm: 7.32 (5H), 1.83 (3H), 1.78 (3H).

$^{13}$CNMR (CDCl$_3$): δppm: 149.0 (C═O), 143.4; 133.4 (═CH Ph), 128.9; 128.6; 128.3; 123.6 (Me$_2$ C═) 19.6; 18.2 (Me).

EXAMPLE 11

Preparation of 2-methyl propen-1-yl chloroformate of formula

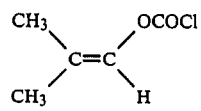

During a period of two hours, 15 grams (0.2 mole) of zinc powder is added to a stirred solution of 14.0 grams (0.13 mole) of alphachloroisobutyraldehyde and 20 cc (0.26 mole) of phosgene in 100 cc of a 2:1 mixture of methyl acetate and ethyl ether. Stirring is continued overnight. Then the excess phosgene is removed under vacuum. There is then added 50 cc of 1-chloro naphthalene and the volatile materials are removed under a pressure of 1 mm of mercury at a temperature of −78° C. The product 2-methyl propen-1-yl chloroformate is isolated by fractional distillation (119° C.–121° C.). The product in the amount of 2.7 grams is obtained in a yield of 15%. The product has the following characteristics:
IR spectrum (CCl$_4$): 3085 cm$^{-1}$, 1780 cm$^{-1}$,
$^1$HNMR (CDCl$_3$): δppm: 7.9–7.6 (1H), 1.8–1.5 (6H).

EXAMPLE 12

Preparation of 1-cyano 2-methyl propen-1-yl chloroformate of formula

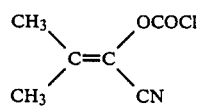

Zinc powder (0.1 gram) is added to a solution of 3.5 cc (0.05 mole) of phosgene in 25 cc of ethyl acetate. After stirring fifteen minutes there is added 4.11 grams (0.023 mole) of 2-bromo 2-methyl propanoyl cyanide and 2.3 grams (0.03 mole) of zinc powder is added over a period of four hours. Stirring is continued for thirty minutes, then the mixture is filtered, washed with 200 cc of dichloromethane, concentrated and distilled (80° C.–83° C. under reduced pressure of 10 mm of mercury).

There is obtained 2.5 grams of 1-cyano 2-methyl propen-1-yl chloroformate (67% yield).
The product has the following properties:
IR spectrum (CCl$_4$): 2180 cm$^{-1}$, 1780 cm$^{-1}$,
$^1$HNMR (CDCl$_3$): δppm: 2.09 (3H), 1.90 (3H).

EXAMPLE 13

This example illustrates one application of 2-methyl propen-1-yl 1-(O,O-diethylphosphonato)chloroformate obtained in Example 8 for the synthesis of a vinyl carbamate.

Specifically, the synthesis of N(2-methyl O,O-diethyl-phosphanto propene-1-yl oxycarbonyl) dioctylamine is carried out by reaction of the chloroformate with dioctylamine according to the scheme:

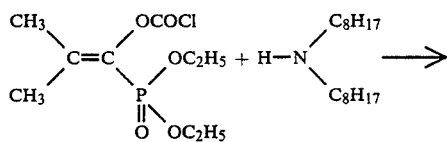

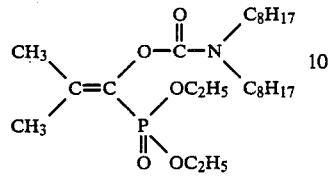

To a solution of 2-methyl propen-1-yl 1-(O-O-diethylphosphonato) chloroformate obtained as described in Example 8 in 10 cc of dichloromethane is added under stirring during the course of thirty minutes a solution of 3.66 grams (0.015 mole) of dioctylamine in 5 cc of dichloromethane.

Stirring is continued for two days and the mixture is then concentrated, diluted with 50 cc of pentane, washed with water (3×10 cc), washed with aqueous dilute 10% hydrochloric acid (4×15 cc), dried over potassium sulfate and reconcentrated. The solution thus obtained is then filtered and the volatile products are removed under vacuum (0.7 mm of mercury) during one hour. There is obtained 1.5 grams (yield 42%) of N(2-methyl 1-O,O-diethylphosphonato propen-1-yl oxycarbonyl) dioctyl amine. The carbamate is obtained as a yellow oil and has the following properties:

IR spectrum (CCl$_4$): 1710 cm$^{-1}$, 1640 cm$^{-1}$, $^1$HNMR (CDCl$_3$): δppm: 4.11 (4H), 3.5–3.0 (4H), 2.11 (3H), 1.73 (3H), 1.8–0.7 (36H).

EXAMPLE 14

This example illustrates the application of 1-(O,O-diethylphosphonato) 2-methyl propen-1-yl chloroformate obtained as described in Example 8, for the synthesis of another vinyl carbamate.

This example relates to the synthesis of N(2-methyl-1-,O,O-diethylphosphonato-propen-1-yl oxycarbonyl) morpholine according to the reaction scheme herein below:

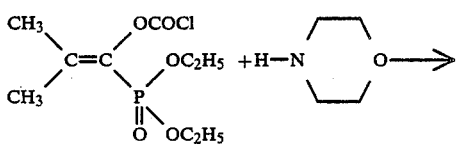

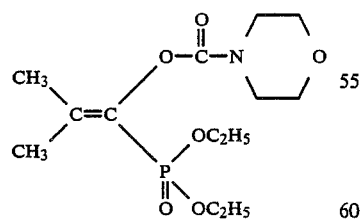

To the compound obtained as described in Example 8,1-(O,O-diethylphosphanato) 2-methyl propen-1-yl chloroformate in 30 cc of ethyl acetate is added 4.56 grams (0.052 mole) of morpholine. The reaction is immediate and the mixture is then filtered. The filtrate is then concentrated and 20 cc of a mixture 2:1 of pentane and dioxane is added to cause the precipitation of the zinc salts. The mixture is filtered again and after concentration 4.3 grams of N(2-methyl, 1-O,O-diethylphosphonato propen-1-yl oxycarbonyl) morpholine is obtained (yield 53%).

The carbamate thus obtained is a viscous oil with the following characteristics:

IR spectrum (CCl$_4$): 1715 cm$^{-1}$, 1645 cm$^{-1}$ $^1$HNMR (CDCl$_3$): δppm: 4.27 (4H), 3.8–3.5 (8H), 2.06 (3H), 1.80 (3H), 1.36 (3H).

What is claimed is:

1. A vinyl chloroformate of formula:

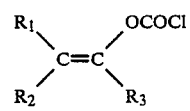

in which:

R$_1$ and R$_2$ are the same or different and each is chlorine, bromine or an alkyl radical, linear or branched, of 1–4 carbon atoms, the radicals R$_1$ and R$_2$ being capable of forming together with the carbon atom to which they are attached a cycloaliphatic ring of 4–8 carbon atoms;

R$_3$ represents:

hydrogen when at least one of R$_1$ and R$_2$ radicals is alkyl;

a linear or branched alkyl of 1–4 carbon atoms or said R$_3$ radical forms with said R$_2$ radical and the carbon atoms to which they are attached an unsubstituted hydrocarbon ring of 5–8 carbon atoms or a hydrocarbon ring of 5–8 carbon atoms substituted by oxygen atoms forming a ketone group in the ring;

an aryl radical which is unsubstituted or substituted by alkyl groups of up to 8 carbon atoms;

the radical cyano—C≡N;

or a phosphonate radical of formula:

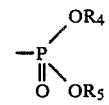

in which R$_4$ and R$_5$ are the same or different, and each is a linear or branched alkyl of 1–4 carbon atoms.

2. The vinyl chloroformate according to claim 1 of formula:

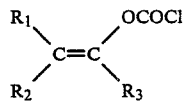

in which

R$_1$ and R$_2$ are the same or different and each is chlorine or a linear or branched alkyl of 1–4 carbon atoms or said radicals R$_1$ and R$_2$ form together with the carbon atom to which they are attached the cyclohexyl ring;

R$_3$ is:

hydrogen when at least one R$_1$ and R$_2$ radicals is alkyl;

methyl;

it forms with $R_2$ and the carbon atoms to which they are attached the cyclohexenyl or oxocyclohexenyl ring;

phenyl;

the cyano—C≡N;

or a phosphonate radical of formula:

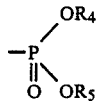

in which $R_4$ and $R_5$ are the same or different and are methyl or ethyl.

3. The process of preparation of a vinyl chloroformate according to claim 1 which comprises reacting phosgene in a solvent in the presence of zinc with an alpha-halogenocarbonyl containing compound of formula:

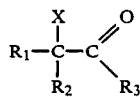

in which:

X is chlorine or bromine;

$R_1$, $R_2$ and $R_3$ are as defined hereinabove.

4. The process according to claim 3 wherein said solvent consists of at least a solvent selected from the group consisting of linear ethers, cyclic ethers and esters.

5. The process according to claim 4 wherein said solvent is a member selected from the group consisting of tetrahydrofuran dioxane, diethyl ether, dimethoxyethane, ethyl acetate and methyl acetate.

6. The process according to claim 4 wherein the solvent is anhydrous.

7. The process according to claim 3 wherein zinc is reacted in at least the stoichiometric amount.

8. The process according to claim 7, wherein zinc is reacted in a molar excess of 5–50% with respect to said alpha halogeno carbonyl containing compound.

9. The process according to claim 7 wherein the zinc is zinc powder, activated zinc or zinc with copper in powder form.

10. The process according to claim 3 wherein the reaction is carried out at a temperature between 0° C. and +60° C.

11. The process according to claim 10 wherein the temperature is between 5° C. and 30° C.

12. The process according to claim 9 wherein the zinc is activated.

* * * * *